United States Patent

Nielsen et al.

[11] Patent Number: 5,834,415
[45] Date of Patent: Nov. 10, 1998

[54] NAPHTHALENE BORONIC ACIDS

[75] Inventors: Lone Kierstein Nielsen, Bagsværd, Denmark; Allison Deane-Wray, Hampshire, Great Britain

[73] Assignee: Novo Nordisk A/S, Novo Alle, Denmark

[21] Appl. No.: 732,339
[22] PCT Filed: Apr. 24, 1995
[86] PCT No.: PCT/DK95/00168
§ 371 Date: Oct. 21, 1996
§ 102(e) Date: Oct. 21, 1996
[87] PCT Pub. No.: WO95/29223
PCT Pub. Date: Nov. 2, 1995

[30] Foreign Application Priority Data

Apr. 26, 1994 [DK] Denmark .................. 0476/94

[51] Int. Cl.[6] .............. C11D 3/386; C11D 3/02
[52] U.S. Cl. ............ 510/392; 510/393; 510/530; 510/226; 510/466; 510/221; 510/321; 510/337
[58] Field of Search ............ 510/392, 393, 510/530, 226, 320, 465, 221, 321, 337; 435/188

[56] References Cited

U.S. PATENT DOCUMENTS

| 5,354,491 | 10/1994 | Bjorkquist et al. | 252/135 |
| 5,422,030 | 6/1995 | Panandiker et al. | 252/135 |
| 5,431,842 | 7/1995 | Panandiker et al. | 252/135 |
| 5,472,628 | 12/1995 | Panandiker et al. | 252/135 |
| 5,488,157 | 1/1996 | Bjorkquist et al. | 562/7 |

FOREIGN PATENT DOCUMENTS

| 0 478 050 A1 | 4/1992 | European Pat. Off. . |
| 2281210 | 3/1995 | United Kingdom . |
| WO 92/19707 | 11/1992 | WIPO . |
| WO 95/02046 | 1/1995 | WIPO . |
| 95/29223 | 11/1995 | WIPO . |
| 96/21716 | 7/1996 | WIPO . |

*Primary Examiner*—Kery A. Fries
*Attorney, Agent, or Firm*—Steve T. Zelson; Elias J. Lombiris

[57] ABSTRACT

A liquid detergent composition comprising a surfactant, an enzyme and a naphthalene boronic acid derivative enzyme stabilizer.

10 Claims, No Drawings

NAPHTHALENE BORONIC ACIDS

CROSS-REFERENCE TO RELATED APPLICATIONS

This application is a 35 U.S.C. 371 national application of PCT/DK95/00168 filed Apr. 25, 1995, which is incorporated herein by reference.

FIELD OF INVENTION

This invention relates to a liquid detergent composition comprising a surfactant, an enzyme and an improved enzyme stabilizer.

BACKGROUND OF THE INVENTION

Storage stability problems are well known with liquids containing enzyme(s). Especially in enzyme-containing liquid detergents a major problem, in particular if the detergent contains protease, is that of ensuring enzyme activity over time.

The prior art has dealt extensively with improving the storage stability, for example by adding a protease inhibitor.

Boric acid and boronic acids are known to reversibly inhibit proteolytic enzymes. A discussion of the inhibition of one serine protease, subtilisin, by boronic acid is provided in *Molecular & Cellular Biochemistry* 51, 1983, pp. 5–32.

Boronic acids have very different capacities as subtilisin inhibitors. Boronic acids containing only alkyl groups such as methyl, butyl or 2-cyclohexylethyl are poor inhibitors with methylboronic acid as the poorest inhibitor, whereas boronic acids bearing aromatic groups such as phenyl, 4-methoxyphenyl or 3,5-dichlorophenyl are very good inhibitors with 3,5-dichlorophenylboronic acid as a particularly effective one (see Keller et al, *Biochem. Biophys. Res. Com.* 176, 1991, pp. 401–405).

It is also claimed that aryl boronic acids which have a substitution at the 3-position relative to boron are unexpectedly good reversible protease inhibitors. Especially, acetamidobenzene boronic acid is claimed to be a superior inhibitor of proteolytic enzymes (see WO 92/19707).

The inhibition constant ($K_i$) is ordinarily used as a measure of capacity to inhibit enzyme activity, with a low $K_i$ indicating a more potent inhibitor. However, it has earlier been found that the $K_i$ values of boronic acids do not always tell how effective inhibitors are (see for instance WO 92/197077).

SUMMARY OF THE INVENTION

In this invention it is surprisingly found that naphthalene boronic acid derivatives have extraordinary good capacities as enzyme stabilizers in liquid detergents.

Accordingly, the present invention relates to a liquid detergent composition comprising a surfactant, an enzyme and a naphthalene boronic acid derivative enzyme stabilizer of the following formula:

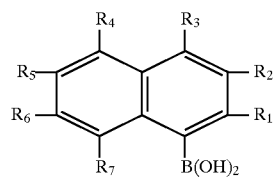

or

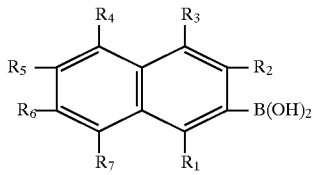

where $R_1$, $R_2$, $R_3$, $R_4$, $R_5$, $R_6$ and $R_7$ is the same or different and selected from hydrogen, $C_1$–$C_6$ alkyl, substituted $C_1$–$C_6$ alkyl, aryl, substituted aryl, hydroxy, hydroxyl derivative, halogen, amine, alkylated amine, amine derivative, nitro, thiol, thiol derivative, aldehyde, acid, acid salt, ester, sulfonate or phosphonate.

DETAILED DISCLOSURE OF THE INVENTION

One embodiment of the present invention provides a liquid detergent composition comprising a surfactant, an enzyme and a naphthalene boronic acid derivative enzyme stabilizer of the following formula:

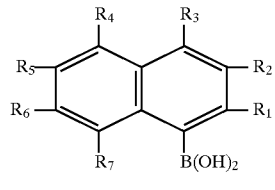

or

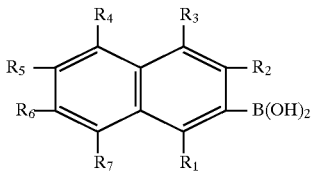

where $R_1$, $R_2$, $R_3$, $R_4$, $R_5$, $R_6$ and $R_7$ is the same or different and selected from hydrogen, $C_1$–$C_6$ alkyl, substituted $C_1$–$C_6$ alkyl, aryl, substituted aryl, hydroxy, hydroxyl derivative, halogen, amine, alkylated amine, amine derivative, nitro, thiol, thiol derivative, aldehyde, acid, acid salt, ester, sulfonate or phosphonate.

A preferred embodiment of the present invention provides a liquid detergent composition comprising a surfactant, an enzyme and a naphthalene boronic acid derivative enzyme stabilizer of the formula disclosed above, wherein at least five of the seven groups ($R_1$–$R_7$) are hydrogen. Preferred examples belonging to this group are dihalogennaphthalene boronic acids such as dichloronaphthalene boronic acids.

A further preferred embodiment of the present invention provides a liquid detergent composition comprising a surfactant, an enzyme and a naphthalene boronic acid derivative enzyme stabilizer of the formula disclosed above, wherein at least six of the seven groups ($R_1$–$R_7$) are hydrogen. Preferred examples belonging to this group are 6-hydroxynaphthalene-2-boronic acid, naphthalene-2-boronic acid and naphthalene-1-boronic acid.

Preparation of Naphthalene Boronic Acid Derivatives

Naphthalene boronic acid derivatives may be prepared using methods well known to those skilled in the art, for example by using a Grignard preparation:

The Grignard reagent is prepared by the slow dropwise addition of the appropriate bromonaphthalene starting material in sodium dried ether to magnesium turnings in sodium dried ether. The reaction is encouraged by the addition of a small iodine crystal.

Trimethylborate or tri-n-butylborate in sodium dried ether is cooled to −70° C. and the Grignard reagent is added dropwise over a period of 2 hours while keeping the borate solution at −70° C. and continuously agitating.

The reaction mixture is allowed to warm to room temperature overnight whereupon it is hydrolysed by the dropwise addition of cold dilute sulphuric acid. The ether layer is separated and the aqueous layer extracted with ether. The ether containing fractions are combined and the solvent removed. The residue is made distinctly alkaline and any methanol or butanol so formed is removed. The alkaline solution is made acidic and cooled and the resulting crystals of desired boronic acid are removed by filtration. All products are preferably recrystallized from distilled water or some other appropriate solvent.

The naphthalene boronic acids may also be prepared using either direct lithiation of the naphthalene and/or lithiation of the bromide.

Any nuclear substitution or protection of functional groups may be achieved by using standard methods well known to those skilled in the art.

Stabilizers

According to the invention the liquid detergent composition may contain up to 500 mM of the stabilizer (the naphthalene boronic acid derivative), preferably the detergent composition may contain 0.001–250 mM of the stabilizer, more preferably the detergent composition may contain 0.005–100 mM of the stabilizer, most preferably the detergent composition may contain 0.01–10 mM of the stabilizer. The naphthalene boronic acid derivative may be an acid or the alkali metal salt of said acid.

Enzymes

According to the invention the liquid detergent composition contains at least one enzyme. The enzyme may be any commercially available enzyme, in particular an enzyme selected from the group consisting of proteases, amylases, lipases, cellulases, oxidoreductases and any mixture thereof. Mixtures of enzymes from the same class (e.g. lipases) are also included.

According to the invention a liquid detergent composition comprising a protease is preferred; more preferred is a liquid detergent composition comprising two enzymes in which the first enzyme is a protease and the second enzyme is selected from the group consisting of amylases, lipases, cellulases and oxidoreductases; even more preferred is a liquid detergent composition in which the first enzyme is a protease and the second enzyme is a lipase.

The amount of enzyme used in the liquid detergent composition varies according to the type of enzyme(s). The amount of each enzyme will typically be 0.2–40 $\mu$M, especially 0.4–20 $\mu$M (generally 5–1000 mg/l, especially 10–500 mg/l) calculated as pure enzyme protein.

Protease: Any protease suitable for use in a detergent composition can be used. Suitable proteases include those of animal, vegetable or microbial origin. Microbial origin is preferred. Chemically or genetically modified mutants are included. It may be a serine protease, preferably an alkaline microbial protease or a trypsin-like protease. Examples of alkaline proteases are subtilisins, especially those derived from Bacillus, e.g. subtilisin Novo, subtilisin Carlsberg, subtilisin 309, subtilisin 147 and subtilisin 168 (described in WO 89/06279). Examples of commercial Bacillus subtilisins are Alcalase®, Savinase®, Esperase® and Durazym® products of Novo Nordisk A/S. Examples of trypsin-like pro-teases are trypsin (e.g. of porcine or bovine origin) and the Fusarium protease described in WO 89/06270.

Amylase: Any amylase suitable for use in a detergent composition can be used. Suitable amylases include those of bacterial and fungal origin. Chemically or genetically modified mutants are included. Amylases include, for example, α-amylases obtained from a special strain of *B. licheniformis*, described in more detail in British Patent Specification No. 1,296,839. Particularly preferred is Termamyl®, available from Novo Nordisk A/S.

Lipase: Any lipase suitable for use in a detergent composition can be used. Suitable lipases include those of bacterial and fungal origin. Chemically or genetically modified mutants are included. Particularly preferred is lipase obtained by cloning the gene from *Humicola lanuginosa* and expressing the gene in *Aspergillus oryzae* as described in EP 0 258 068, available under the trade mark Lipolase® from Novo Nordisk A/S.

Cellulase: Any cellulase suitable for use in a detergent composition can be used. Suitable cellulases include those of bacterial and fungal origin. Chemically or genetically modified mutants are included. Suitable cellulases are disclosed in U.S. Pat. No. 4,435,307. Particularly preferred is Celluzyme™ produced by a strain of *Humicola insolens*, available from Novo Nordisk A/S.

Oxidoreductases: Any oxidoreductase suitable for use in a detergent composition, e.g., peroxidases and oxidases such as laccases, can be used herein. Suitable peroxidases herein include those of plant, bacterial and fungal origin. Chemically or genetically modified mutants are included. Examples of suitable peroxidases are those derived from a strain of Coprinus, e.g. *C. cinerius* or *C. macrorhizus*, or from a strain of Bacillus, e.g. *B. pumilus*, particularly peroxidase according to PCT/DK 90/00260.

Deterrents

According to the invention the liquid detergent composition will beside enzyme(s) and stabilizer comprise a surfactant. The detergent composition may, e.g., be a laundry detergent composition or a dishwashing detergent composition.

The detergent may be aqueous, typically containing up to 70% water and 0–30% organic solvent, or nonaqueous.

The detergent composition comprises one or more surfactants, each of which may be anionic, nonionic, cationic, or amphoteric (zwitterionic). The detergent will usually contain 0–50% of anionic surfactant such as linear alkylbenzene-sulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), alcohol propoxylate, carboxylated alcohol ethoxylates, nonylphenol ethoxylate, alkylpolygly-coside, alkyldimethylamine oxide, ethoxylated fatty acid monoethanolamide, fatty acid monoethanolamide, or polyhydroxy alkyl fatty acid amide (e.g. as described in WO 92/06154).

Normally the detergent contains 1–65% of a detergent builder, but some dishwashing detergents may contain even up to 90% of a detergent builder, or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst).

The detergent builders may be subdivided into phosphorus-containing and non-phosphorous-containing types. Examples of phosphorus-containing inorganic alkaline detergent builders include the water-soluble salts, especially alkali metal pyrophosphates, orthophosphates, polyphosphates and phosphonates. Examples of non-phosphorus-containing inorganic builders include water-soluble alkali metal carbonates, borates and silicates as well as layered disilicates and the various types of water-insoluble crystalline or amorphous alumino silicates of which zeolites is the best known representative.

Examples of suitable organic builders include alkali metal, ammonium or substituted ammonium salts of succinates, malonates, fatty acid malonates, fatty acid sulphonates, carboxymethoxy succinates, polyacetates, carboxylates, polycarboxylates, aminopolycarboxylates and polyacetyl carboxylates.

The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, polymaleates, maleic/acrylic acid copolymers and lauryl methacrylate/acrylic acid copolymers.

The detergent composition may contain bleaching agents of the chlorine/bromine-type or the oxygen-type. The bleaching agents may be coated or encapsulated. Examples of inorganic chlorine/bromine-type bleaches are lithium, sodium or calcium hypochlorite or hypobromite as well as chlorinated trisodium phosphate. The bleaching system may also comprise a $H_2O_2$ source such as perborate or percarbonate which may be combined with a peracid-forming bleach activator such as tetraacetylethylenediamine (TAED) or nonanoyloxybenzene-sulfonate (NOBS).

Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water solubilizing cations such as potassium and sodium. Hydantoin compounds are also suitable. The bleaching system may also comprise peroxyacids of, e.g., the amide, imide, or sulfone type.

In dishwashing detergents the oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED or NOBS.

The enzyme(s) of the detergent composition of the invention may additionally be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, deflocculant material, foam boosters/foam depressors (in dishwashing detergents foam depressors), suds suppressors, anti-corrosion agents, soil-suspending agents, anti-soil-redeposition agents, dyes, dehydrating agents, bactericides, optical brighteners, or perfume.

The pH (measured in aqueous solution at use concentration) will usually be neutral or alkaline, e.g. in the range of 7–11.

Particular forms of laundry detergent compositions within the scope of the invention include:

1) An aqueous liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO or $C_{12-15}$ alcohol, 5 EO) | 12–18% |
| Soap as fatty acid (e.g. oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g. PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g. dispersants, suds suppressors, perfume, optical brightener) | 0–5% |

2) An aqueous structured liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO, or $C_{12-15}$ alcohol, 5 EO) | 3–9% |
| Soap as fatty acid (e.g. oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g. PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g. dispersants, suds suppressors, perfume, optical brighteners) | 0–5% |

3) An aqueous liquid detergent composition comprising

| | |
|---|---|
| Linear alkylbenzenesulfonate (calculated as acid) | 15–23% |
| Alcohol ethoxysulfate (e.g. $C_{12-15}$ alcohol, 2–3 EO) | 8–15% |
| Alcohol ethoxylate (e.g. $C_{12-15}$ alcohol, 7 EO, or $C_{12-15}$ alcohol, 5 EO) | 3–9% |
| Soap as fatty acid (e.g. lauric acid) | 0–3% |
| Aminoethanol | 1–5% |
| Sodium citrate | 5–10% |
| Hydrotrope (e.g. sodium toluensulfonate) | 2–6% |
| Borate (as $B_4O_7$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g. polymers, dispersants, perfume, optical brighteners) | 0–5% |

4) An aqueous liquid detergent composition comprising

| | |
|---|---|
| Linear alkylbenzenesulfonate (calculated as acid) | 20–32% |
| Alcohol ethoxylate (e.g. $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g. maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g. hydrotropes, dispersants, perfume, optical brighteners) | 0–5% |

5) Detergent formulations as described in 1)–4) wherein all or part of the linear alkylbenzenesulfonate is replaced by $(C_{12}–C_{18})$ alkyl sulfate.

6) Detergent formulations as described in 1)–5) which contain a stabilized or encapsulated peracid, either as an additional component or as a substitute for already specified bleach systems.

7) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

Particular forms of dishwashing detergent compositions within the scope of the invention include:

1) LIQUID DISHWASHING COMPOSITION WITH CLEANING SURFACTANT SYSTEM

| | |
|---|---|
| Nonionic surfactant | 0–1.5% |
| Octadecyl dimethylamine N-oxide dihydrate | 0–5% |
| 80:20 wt. C18/C16 blend of octadecyl dimethylamine N-oxide dihydrate and hexadecyldimethyl amine N-oxide dihydrate | 0–4% |
| 70:30 wt. C18/C16 blend of octadecyl bis (hydroxyethyl) amine N-oxide anhydrous and hexadecyl bis (hydroxyethyl) amine N-oxide anhydrous | 0–5% |
| $C_{13}–C_{15}$ alkyl ethoxysulfate with an average degree of ethoxylation of 3 | 0–10% |
| $C_{12}–C_{15}$ alkyl ethoxysulfate with an average degree of ethoxylation of 3 | 0–5% |
| $C_{13}–C_{15}$ ethoxylated alcohol with an average degree of ethoxylation of 12 | 0–5% |
| A blend of $C_{12}–C_{15}$ ethoxylated alcohols with an average degree of ethoxylation of 9 | 0–6.5% |
| A blend of $C_{13}–C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |
| Sodium perborate monohydrate | 0–11.5% |
| Tetraacetylethylenediamine (TAED) | 0–4% |
| Maleic acid/acrylic acid copolymer | 0–7.5% |
| Sodium sulphate | 0–12.5% |
| Enzymes | 0.0001–0.1% |

2) NON-AQUEOUS LIQUID AUTOMATIC DISHWASHING COMPOSITION

| | |
|---|---|
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher glycols, polyglycols, polyoxides, glycolethers | 25.0–45.0% |
| Stabilizer (e.g. a partial ester of phosphoric acid and a $C_{16}–C_{18}$ alkanol) | 0.5–7.0% |
| Foam suppressor (e.g. silicone) | 0–1.5% |
| Enzymes | 0.0001–0.1% |

3) NON-AQUEOUS LIQUID DISHWASHING COMPOSITION

| | |
|---|---|
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |
| Low molecule weight polyacrylate polymer | 5.0–15.0% |
| Clay gel thickener (e.g. bentonite) | 0.0–10.0% |
| Hydroxypropyl cellulose polymer | 0.0–0.6% |
| Enzymes | 0.0001–0.1% |
| Liquid carrier selected from higher lycols, polyglycols, polyoxides and glycol ethers | Balance |

4) THIXOTROPIC LIQUID AUTOMATIC DISHWASHING COMPOSITION

| | |
|---|---|
| $C_{12}–C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminum tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decydiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes | 0.0001–0.1% |
| Suds suppressor, dye, perfumes, water | Balance |

5) LIQUID AUTOMATIC DISHWASHING COMPOSITION

| | |
|---|---|
| Alcohol ethoxylate | 0–20% |
| Fatty acid ester sulphonate | 0–30% |
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |

-continued

| | |
|---|---|
| Sodium perborate monohydrate | 0–13% |
| Tetraacetylethylenediamine (TAED) | 0–8% |
| Maleic acid/acrylic acid copolymer | 0–8% |
| Enzymes | 0.0001–0.1% |

6) LIQUID AUTOMATIC DISHWASHING COMPOSITION CONTAINING PROTECTED BLEACH PARTICLES

| | |
|---|---|
| Sodium silicate | 5–10% |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |
| Enzymes | 0.0001–0.1% |
| Water | Balance |

7) Automatic dishwashing compositions as described in 1) and 5), wherein perborate is replaced by percarbonate. 8) Automatic dishwashing compositions as described in 1), which additionally contain a manganese catalyst. The manganese catalyst may, e.g., be one of the compounds described in "Efficient manganese catalysts for low-temperature bleaching", Nature 369, 1994, pp. 637–639.

Tests of Stabilizers

According to the invention the effectiveness of each stabilizer may be tested in one or more of the following three tests:

a) Storage Stability Test in Liquid Deterrent: Enzyme(s) and stabilizer are added to a liquid detergent formulation and stored at well defined conditions. The enzyme activity of each enzyme is determined as a function of time, e.g. after 0, 3, 7 and 14 days.

To calculate the inhibition efficiency from the storage stability date a reaction mechanism is proposed. The following reactions give a relatively simple, but yet plausible, mechanism for a liquid detergent containing protease (P), lipase (L), and inhibitor (I):

I) Autodigestion of protease:

$P+P \rightarrow D_P+P$ 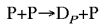

II) Denaturation of protease:

$P \rightarrow D_P$ 

III) Inhibition of protease:

$P+I \leftrightharpoons PI$ 

IV) Protease digestion of inhibited enzyme:

$P+PI \rightarrow P+D_P+I$ 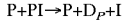

V) Denaturation of inhibited enzyme:

$PI \rightarrow D_P+I$ 

VI) Protease digestion of lipase:

$P+L \rightarrow P+D_L$ 

VII) Denaturation of lipase:

$L \rightarrow D_L$ 

where $D_P$ and $D_L$ are denatured (i.e. non-active) protease and lipase.

From these reactions three coupled differential equations are derived describing the deactivation of P, L and PI. The reaction rate constants are derived from storage stability data by the use of a parameter estimation method (Gauss-Newton with the Levenberg modification). The storage stability data give the concentration of (P+PI) and L as a function of time.

Reaction III is much faster than the other reactions and equilibrium is assumed in the calculations. Reaction IV is excluded from the system to reduce the number of parameters thereby describing the stability of the inhibited enzyme by only one reaction rate constant (from equation V).

In all experiments there is a large surplus of inhibitor molecules compared to protease molecules, i.e. a constant concentration of inhibitor (corresponding to the added amount of inhibitor) is a reasonable assumption.

The specific values of the reaction rate constants are somewhat sensitive to small variations in the data, but the sensitivity is reduced significantly by giving the results relatively to the value from Boric Acid. An improvement factor is thus derived:

$$IF_I = \frac{K_I(\text{Boric Acid})}{K_I(\text{Inhibitor})}$$

$IF_1$ measures the inhibition efficiency given by the inhibition constants $K_i$ from reaction III.

b) The "Milk" Test: In this test the stabilizer to be tested is compared with a reference inhibitor (boric acid). The test is described in details below:

Preparation of "inhibitor" milk: 0.075 g of $CaCl_2$ (dried fine-granular pure, Merck), 0.16 g of 3,3-dimethylglutaric acid (SIGMA) and 2.5 mmole of stabilizer/inhibitor are weighed out and dissolved in 50 ml of demineralised water. pH is adjusted to approx. 6.0 with NaOH. 6.0 g of skimmed milk powder (dehydrated, DIFCO Lab.) is weighed out in a 100 ml beaker, and the solution of salt+buffer+stabilizer/inhibitor is added. This mixture is stirred heavily for some minutes to be sure that all lumps, if any, are apart. Thereafter the mixture is stirred for 30 minutes. pH is adjusted to 6.50 with NaOH. Skimmed milk from a bottle can be used instead of powder. Use milk from the same bottle for all stabilizers/inhibitors in one run.

Preparation of the enzyme: Prepare a solution of approx. 30 KNPU/litre of Savinase® (available from Novo Nordisk A/S) in boric acid buffer (see below). The Savinase activity is determined relatively to an enzyme standard. A folder AF 220/1-GB describing the analytical method of determining the Savinase activity is available upon request to Novo Nordisk A/S, Denmark, which folder is hereby included by reference.

Example: 1.0 g of 16 KNPU/g liquid Savinase is weighed out and 50 ml of boric acid buffer are added. The mixture is stirred for 15 minutes. 10 ml of this solution are filled into a 100 ml beaker, and boric acid buffer is added up to 100 ml. Thereafter the mixture is stirred for 15 minutes. Boric acid buffer: 2.5 g of boric acid (Merck) are dissolved in 500 ml of demineralised water. pH is adjusted to 9.0 with NaOH.

The curdling: 10.0 ml of stabilizer/inhibitor are added to a test tube. 3 test tubes of each stabilizer/inhibitor are made and placed in a 30° C. water bath. The test tubes are left in the water bath for one hour. 1.00 ml of Savinase solution is added to the test tube and the stop-watch is started. The tube is mixed for 10 seconds on the "vibrator" and thereafter placed in the water bath. When the curdling starts the stop-watch is stopped. The deviation between the curdling time for the three test tubes should not be more than approx. 10 seconds. How and when the curdling starts must be learned in practice and the same person should curdle all samples. The curdling time for the reference inhibitor (boric acid) should be around 3–4 minutes (if the curdling time is longer, a stronger protease solution should be used). The curdling time is approx. linear proportional to 1/ (protease activity). The result can be reported as an improvement factor IF defined by: (curdling time stabilizer)/(curdling time reference).

c) Determination of $K_i$: The inhibition constant $K_i$ may be determined by using standard methods, for reference see Keller et al, *Biochem. Biophys. Res. Com.* 176, 1991, pp.401–405; J. Bieth in *Bayer-Symposium "Proteinase Inhibitors"*, pp. 463–469, Springer-Verlag, 1974 and Lone Kierstein Hansen in "*Determination of Specific Activities of Selected Deterrent Proteases using Protease Activity, Molecular Weights, Kinetic Parameters and Inhibition Kinetics*", PhD-report, Novo Nordisk A/S and University of Copenhagen, 1991.

The invention is further illustrated in the following examples which are not intended to be in any way limiting to the scope of the invention as claimed.

EXAMPLE 1
Preparation of Naphthalene-1-Boronic Acid

The Grignard reagent was prepared by the slow dropwise addition of 1-bromonaphthalene (0.05 m) in sodium dried ether (50 ml) to magnesium turnings (0.05 m) in sodium dried ether (50 ml). The reaction was encouraged by the addition of a small iodine crystal.

Trimethylborate (0.05 m) or tri-n-butylborate (0.05 m) in sodium dried ether was cooled to −70° C. and the Grignard reagent was added dropwise over a period of 2 hours while keeping the borate solution at −70° C. and continuously agitating.

The reaction mixture was allowed to warm to room temperature overnight whereupon it was hydrolysed by the dropwise addition of cold dilute sulphuric acid (10%, 50 ml). The ether layer was separated and the aqueous layer extracted with ether. The ether containing fractions were combined and the solvent removed. The residue was made distinctly alkaline and any methanol or butanol so formed was removed. The alkaline solution was made acidic and cooled and the resulting crystals were removed by filtration. The combined boronic acid crystals were recrystallized from distilled water. $C_{10}H_9BO_2$, mpt. 210°–211° C.

Preparation of Naphthalene-2-Boronic Acid

2-Naphthalene Boronic Acid was made in the same way as 1-Naphthalene Boronic Acid, only 2-bromonaphthalene was used instead of 1-bromonaphthalene. $C_{10}H_9BO_2$, mpt. 258°–259°C.

Protection of 6-hydroxy-2-bromonaphthalene in order to make 6-hydroxynaphthalene-2-boronic acid 6-hydroxy-2-bromonaphthalene (0.05M) was dissolved in dichloromethane (50 ml). Dihydropyran (7.5 ml) was added along with a small amount of p-toluene sulphonic acid to catalyse the reaction. The mixture was stirred at 25° C. for 3 hours.

The solution was then basified by the addition of an ammonical methanol solution (1:5, 30 ml). The solvents were removed and the remaining brown residue was dissolved in dichloromethane (30 ml) and extracted with sodium carbonate solution (0.1M, 2×30 ml).

The organic layer was dried over anhydrous sodium sulphate and the solvent removed. The resulting protected bromide was then used in the Grignard reaction to make 6-hydroxynaphthalene-2-boronic acid.

EXAMPLE 2
Determination of $K_i$

The inhibition constant $K_i$ for the inhibition of Alcalase and Savinase was determined using standard methods under the following conditions:

Substrate: Succinyl-Alanine-Alanine-Proline-Phenylalanine-paranitro-anilide=SAAPFpNA (Sigma S-7388).

Buffer: 0.1M Tris-HCl pH 8.6; 25° C.

Enzyme concentration in assay:
Alcalase: $1\times10^{-10}$–$3\times10^{-10}$M
Savinase: $1\times10^{-10}$–$3\times10^{-10}$M The initial rate of substrate hydrolysis was determined at nine substrate concentrations in the range of 0.01 to 2 mM using a Cobas Fara automated spectrophotometer. The kinetic parameters $V_{max}$ and $K_m$ were determined using ENZFITTER (a non-linear regression data analysis program). $k_{cat}$ was calculated from the equation $V_{max}=k_{cat}\times[E_o]$. The concentration of active enzyme $[E_o]$ was determined by active site titration using tight-binding protein proteinase inhibitors. The inhibition constant $K_i$ was calculated from plots of $K_m/k_{cat}$ as a function of the concentration of inhibitor. The inhibitors were assumed to be 100% pure and the molar concentrations were determined using weighing numbers and molecular weights.

The results of the inhibition constants $K_i$ of the boronic and borinic acid derivative enzyme stabilizers tested are listed in

TABLE 1

The inhibition constants for the inhibition of Alcalase and Savinase by naphthalene boronic acids. Boric acid is included for comparison.

| Inhibitor | $K_i$ Alcalase | $K_i$ Savinase |
|---|---|---|
| Boric acid | 30 mM | 20 mM |
| Naphthalene-2-boronic acid | 0.4 mM | 0.3 mM |
| Naphthalene-1-boronic acid | 0.5 mM | 0.9 mM |
| 6-hydroxy-naphthalene-2-boronic acid | 0.5 mM | 0.6 mM |

EXAMPLE 3
Storage Stability Test in Liquid Detergent

Naphthalene boronic acids were also tested in storage stability tests in liquid detergents using the method described previously under the following conditions:

Deterrent base (US-type)

| | % wt (as pure components) |
|---|---|
| Nansa 1169/p | 10.3 (Linear Alkylbenzene Sulfonate, LAS) |
| Berol 452 | 3.5 (Alkyl Ether Sulfate, AES) |
| Oleic acid | 0.5 |
| Coconut fatty acid | 0.5 |
| Dobanol 25-7 | 6.4 (Alcohol Ethoxylate, AEO) |
| Sodium xylene sulfonate | 5.1 |
| Ethanol | 0.7 |
| MPG | 2.7 (Mono Propylene Glycol) |
| Glycerol | 0.5 |
| Sodium sulfate | 0.4 |
| Sodium carbonate | 2.7 |
| Sodium citrate | 4.4 |
| Citric acid | 1.5 |
| Water | 60.8 |

-continued

| | % wt (as pure components) |
|---|---|
| Enzyme dosage: | 1% w/w Savinase (14 KNPU/g) |
| Enzyme Stabilizer Dosage: | 5 mmole/kg (for boric acid 160 mmole/kg) |
| Storage: | 0, 3, 7 and 14 days at 30° C. |

The results of the inhibition effectiveness $IF_1$ of the naphthalene boronic acid enzyme stabilizers tested are listed below.

TABLE 2 shows the results of different naphthalene boronic acids and the corresponding $IF_1$. Boric acid is included for comparison.

| Inhibitor | Improvement Factor $IF_I$ |
|---|---|
| Boric acid | 1 |
| Naphthalene-2-boronic acid | 30 |
| Naphthalene-1-boronic acid | 5 |
| 6-hydroxynaphthalene-2-boronic acid | 26 |

Comparing the results of Table 1 ($K_i$ Savinase) with the results of Table 2 it seems that the effect of a naphthalene boronic acid stabilizer in detergents can be predicted from the results obtained in buffer systems and vice versa.

We claim:

1. A liquid detergent composition comprising a surfactant, an enzyme and a naphthalene boronic acid derivative enzyme stabilizer of the following formula:

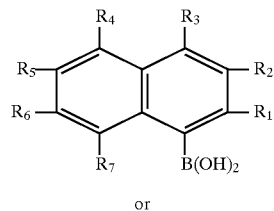

or

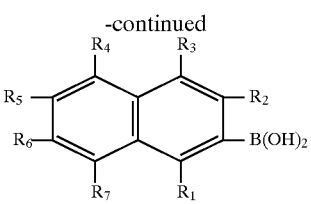

where $R_1$, $R_2$, $R_3$, $R_4$, $R_5$, R6 and $R_7$ is the same or different and selected from hydrogen, $C_1$–$C_6$ alkyl, aryl, hydroxy, halogen, amine, alkylated amine, nitro, thiol, aldehyde, acid, acid salt, ester, sulfonate or phosphonate.

2. The liquid detergent composition according to claim 1, wherein the naphthalene boronic acid derivative enzyme stabilizer is naphthalene-2-boronic acid, naphthalene-1-boronic acid or 6-hydroxynaphthalene-2-boronic acid.

3. The liquid detergent composition according to claim 1, wherein the enzyme is a protease.

4. The liquid detergent composition according to claim 1, additionally comprising a detergent-compatible second enzyme selected from the group consisting of an amylase, a lipase, a cellulase, an oxidoreductase, and any mixture thereof.

5. The liquid detergent composition according to claim 4, wherein the second enzyme is a lipase.

6. The liquid detergent composition according to claim 1, wherein said naphthalene boronic acid derivative enzyme stabilizer is the alkali metal salt of the boronic acid.

7. The liquid detergent composition according to claim 1, wherein said naphthalene boronic acid derivative enzyme stabilizer is added in an amount of up to 500 mM.

8. The liquid detergent composition according to claim 7, wherein said naphthalene boronic acid derivative enzyme stabilizer is added in an amount of 0.001–250 mM.

9. The liquid detergent composition according to claim 8, wherein said naphthalene boronic acid derivative enzyme stabilizer is added in an amount of 0.005–100 mM.

10. The liquid detergent composition according to claim 9, wherein said naphthalene boronic acid derivative enzyme stabilizer is added in an amount of 0.01–10 mM.

* * * * *

UNITED STATES PATENT AND TRADEMARK OFFICE
CERTIFICATE OF CORRECTION

PATENT NO. : 5,834,415

DATED : November 10, 1998

INVENTOR(S) : Nielsen et al.

It is certified that error appears in the above-identified patent and that said Letters Patent is hereby corrected as shown below:

Col. 14, line 10, claim 1:   change "R6" and insert --$R_6$--

Signed and Sealed this

Thirtieth Day of November, 1999

Attest:

Q. TODD DICKINSON

*Attesting Officer*   *Acting Commissioner of Patents and Trademarks*